United States Patent
Nøsted et al.

[11] Patent Number: 6,059,107
[45] Date of Patent: May 9, 2000

[54] URINARY CATHETER ASSEMBLY WITH A READY-TO-USE CATHETER

[75] Inventors: Ulrik Nøsted, Lyngby; Jan Torstensen, Virum; Helle Kayerød, Copenhagen N; Allan Tanghøj, Kokkedal, all of Denmark

[73] Assignee: Coloplast A/S, Denmark

[21] Appl. No.: 09/297,150

[22] PCT Filed: Sep. 18, 1997

[86] PCT No.: PCT/DK97/00395

§ 371 Date: Apr. 26, 1999

§ 102(e) Date: Apr. 26, 1999

[87] PCT Pub. No.: WO98/19729

PCT Pub. Date: May 14, 1998

[30] Foreign Application Priority Data

Nov. 1, 1996 [DK] Denmark ................... 1224/96

[51] Int. Cl.[7] .................................................. B65D 85/08
[52] U.S. Cl. ........................... 206/364; 206/210; 604/265
[58] Field of Search .................................. 206/205, 210, 206/364, 438, 484, 484.2; 604/171, 172, 263, 265

[56] References Cited

U.S. PATENT DOCUMENTS

| | | |
|---|---|---|
| 3,035,691 | 5/1962 | Rasmussen et al. . |
| 3,648,704 | 3/1972 | Jackson . |
| 3,934,721 | 1/1976 | Juster et al. ........................... 206/364 |
| 3,967,728 | 7/1976 | Gordon et al. . |
| 4,204,527 | 5/1980 | Wu et al. . |
| 4,379,506 | 4/1983 | Davidson . |
| 5,226,530 | 7/1993 | Golden . |
| 5,447,231 | 9/1995 | Kastenhofer ........................... 206/364 |
| 5,454,798 | 10/1995 | Kubalak et al. . |
| 5,497,601 | 3/1996 | Gonzalez ........................... 206/364 |
| 5,895,374 | 4/1999 | Rodsten ........................... 206/364 |

FOREIGN PATENT DOCUMENTS

| | | |
|---|---|---|
| 021771B1 | 12/1991 | European Pat. Off. . |
| 0586324A1 | 3/1994 | European Pat. Off. . |
| 0677299A1 | 4/1994 | European Pat. Off. . |
| 2284764 | 6/1995 | United Kingdom . |
| 94/16747 | 8/1994 | WIPO . |
| 96/30277 | 10/1996 | WIPO . |

*Primary Examiner*—Paul T. Sewell
*Assistant Examiner*—Luan K. Bui
*Attorney, Agent, or Firm*—Ostrolenk, Faber, Gerb & Soffen, LLP

[57] ABSTRACT

A urinary catheter assembly comprises a urinary catheter (1) having on at least a part of its surface a hydrophilic surface layer (6) intended to produce a low-friction surface character of the catheter by treatment with a liquid swelling medium prior to use of the catheter and a catheter package (7) having a cavity (11) for accommodation of the catheter (1). The package (7) is made with walls of a gas impermeable material to accommodate a catheter pretreated with said liquid swelling medium for long time preservation of said low-friction surface character and provision of a ready-to-use catheter assembly.

10 Claims, 2 Drawing Sheets

U.S. Patent    May 9, 2000    Sheet 1 of 2    6,059,107
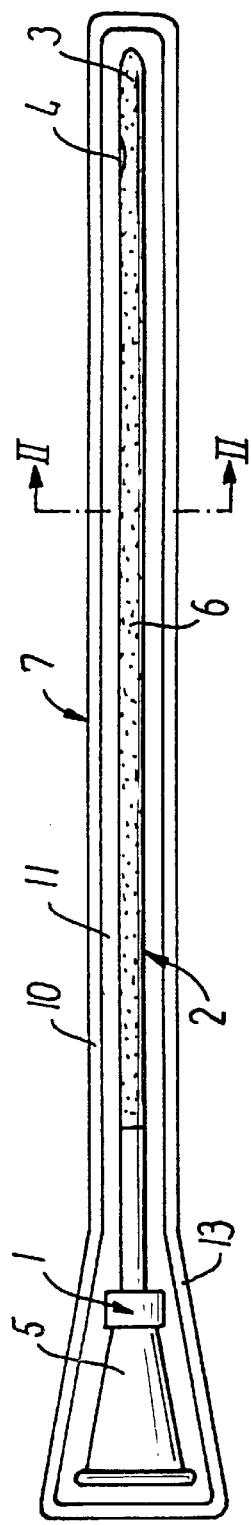
FIG. 1
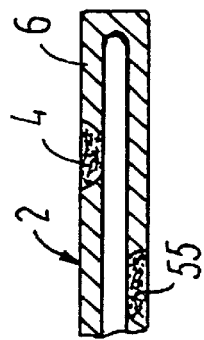
FIG. 4
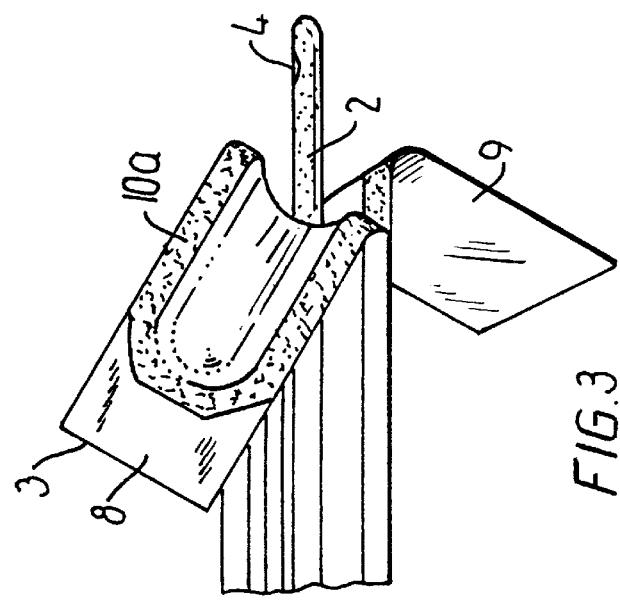
FIG. 3
FIG. 2

URINARY CATHETER ASSEMBLY WITH A READY-TO-USE CATHETER

This invention related to a Urinary catheter assembly comprising a urinary catheter having on at least a part of its surface a hydrophilic surface layer intended to produce a low-friction surface character of the catheter by treatment with a liquid swelling medium prior to use of the catheter and a catheter package having a cavity for accommodation of the catheter.

Urinary catheters of the kind to which the invention pertains are known, inter alia, from EP-A-0 217 771, EP-A-0 586 324 and WO 94/16747, whereas various forms of catheter packages are known from U.S. Pat. Nos. 3,035,691, 3,648,704, 3,967,728, 4,204,527, 4,379,506, 5,226,530, 5,454,798, GB-A-2,284,764, EP-A-0 677 299 and DK Design Registration No. 0932 1986.

U.S. Pat. Nos. 3,648,704, 3,967,728, GB-A-2,284,764 and EP-A-0 677 299 discloses a conventional urinary catheter assembly comprising a catheter of the kind where prior to insertion of the catheter into the urethra the tip of the catheter is to be lubricated with a gel-like lubricant and a package where such a lubricant is accommodated in a rupturable pouch connected or located within the package itself adjacent to the tip of the catheter or is supplied together with the catheter package for connection therewith prior to use of the catheter.

U.S. Pat. No. 5,226,530 discloses a prelubricated catheter and package assembly, in which a urinary catheter prelubricated with a conventional lubricant is accommodated in a package comprising a first receptacle for stowing the catheter and inside said receptacle a secondary receptacle for receiving the projecting or distal end of the catheter to the tip of which the lubricant is applied. The two receptacles are wrapped in an outside enclosing receptacle the contents of which can be sterilized in a suitable manner.

The use of a sequence of three receptacles which must all be opened before use of the catheter makes the operation unduly difficult for disabled users, such as tetraplegics or sclerosis patients.

An important feature of any urinary catheter used for intermittent catherisation of the bladder of an incontinent user is the ability of the catheter to slide easily through the urethra without exposing the urethral walls to any risk of damage. Catheters of the kind to which the inventions pertains have been developed to meet this need by imparting an extremely low friction character to at least the part of the surface of the catheter which is actually introduced into the urethra. The low friction surface character is obtained by incorporating into the relevant part of the catheter at least a hydrophilic surface layer, typically in the form of a coating, and exposing this layer or coating to contact with a liquid swelling medium immediately prior to use.

In order to maintain the low friction surface character during location of the catheter in the urethra and subsequent withdrawal therefrom and hereby reduce stinging pain it is further known to incorporate an osmolality promoting agent, such as NaCl, in the hydrophilic coating.

When catheters of this kind are used directly by end users outside the medical environment of a hospital or a clinic, e.g. by tetraplegic patients who often have a very poor dexterity, and therefore need a very simple insertion procedure, the most common liquid swelling medium used for preparation of the catheter immediately prior to use would be normal tap water.

In order to reduce the risk of infection inherent with the performance of intermittent catherisation of the bladder both the actual swelling medium used and the environment in which the catherisation is performed need, however, to be as clean and antiseptic as possible. Evidently, this need may be very difficult to meet in many daily life situations, as where catherisation must be performed outside the users normal daily environment, e.g. in public toilets, where neither the water supply nor the general state of cleanliness can be expected to be of a sufficiently high standard. Moreover, many disabled users have severe difficulties in entering available toilet rooms due to simple physical barriers like narrow access ways, stairs and the like.

From W0 96/30277 a catheter assembly of the kind defined above comprising a urinary catheter with a hydrophillic surface coating and a package for accommodation of the catheter has been disclosed, by which the preparation of the catheter for use by designing the package itself to be used as a container for the catheter during the wetting operation immediately prior to use. In this design the package is formed from two walls welded together along their edges so as to permit initial local separation of the walls in one end of the package only for inlet and subsequent removal of a wetting agent further permit the package itself to function as an insertion applicator after completion of the wetting operation.

Although this known catheter assembly significantly facilitates the preparation and insertion of the catheter, the manipulations required by the user to perform the wetting an application operations are still to cumbersome for the above-mentioned users having a very poor dexterity.

On this background, it is the object of the invention to improve and facilitate the performance of intermittent urinary catherisation in any type of environment by providing a ready to use urinary catheter assembly comprising a catheter on withdrawal from its package is already prepared for direct insertion in the urethra and in a substantially sterile condition, whereby operation of the catheter assembly is further facilitated and the general quality of life for users of intermittent catherisation would be greatly improved.

In order to meet this and other objects of the invention, as set forth in the following, a urinary catheter according to the invention is characterised in that the package is formed with walls made throughout of a gas impermeable material for long time accommodation of said at least one urinary catheter, said catheter having been pretreated with said liquid swelling medium before arrangement in said package for long time preservation of said low-friction surface character during accommodation in said package and provision of a ready-to-use catheter assembly.

The term "gas impermeable" material should be understood in this context to mean any material that will be sufficiently tight against diffusion by evaporation of the actual liquid swelling medium for a period exceeding the recommended shelf life time of the catheter assembly which could be up to five years, typically 36 months.

Thereby, preparation of the catheter with the liquid swilling medium prior to use is avoided, so that the catheter is ready for insertion into the urethra immediately upon withdrawal for the package which can be designed for easy opening and withdrawal of the catheter.

Thus, the joint between the two sheets of film material of the package may advantageously be a welded joint which may be formed to allow easy opening of the package for withdrawal of the prepared catheter.

Such a welded joint may comprise a part provided as a peelable joint permitting separation of said sheets from each other for withdrawal of said catheter from the package.

In order to reduce the amount of liquid swelling medium required for activation of the hydrophilic surface coating of the catheter, the latter may advantageously be provided with means preventing said swelling medium from getting into contact with internal or external surface parts of the catheter not provided with said hydrophilic layer for an activation period during which said medium is applied to the surface part provided with said hydrophilic layer.

In the following, the invention will be explained in more detail by means of an embodiment illustrated in the accompanying drawings, in which FIGS. 1 and 2 are an upper plan view and a cross-sectional view, respectively, of an embodiment of a urinary catheter assembly according to the invention;

FIG. 3 illustrates opening of a catheter package as shown in FIGS. 1 and 2;

FIG. 4 illustrates a part of a catheter provided with means to reduce the amount of liquid swelling medium required for activation of a hydrophilic surface coating.

Figure 5:
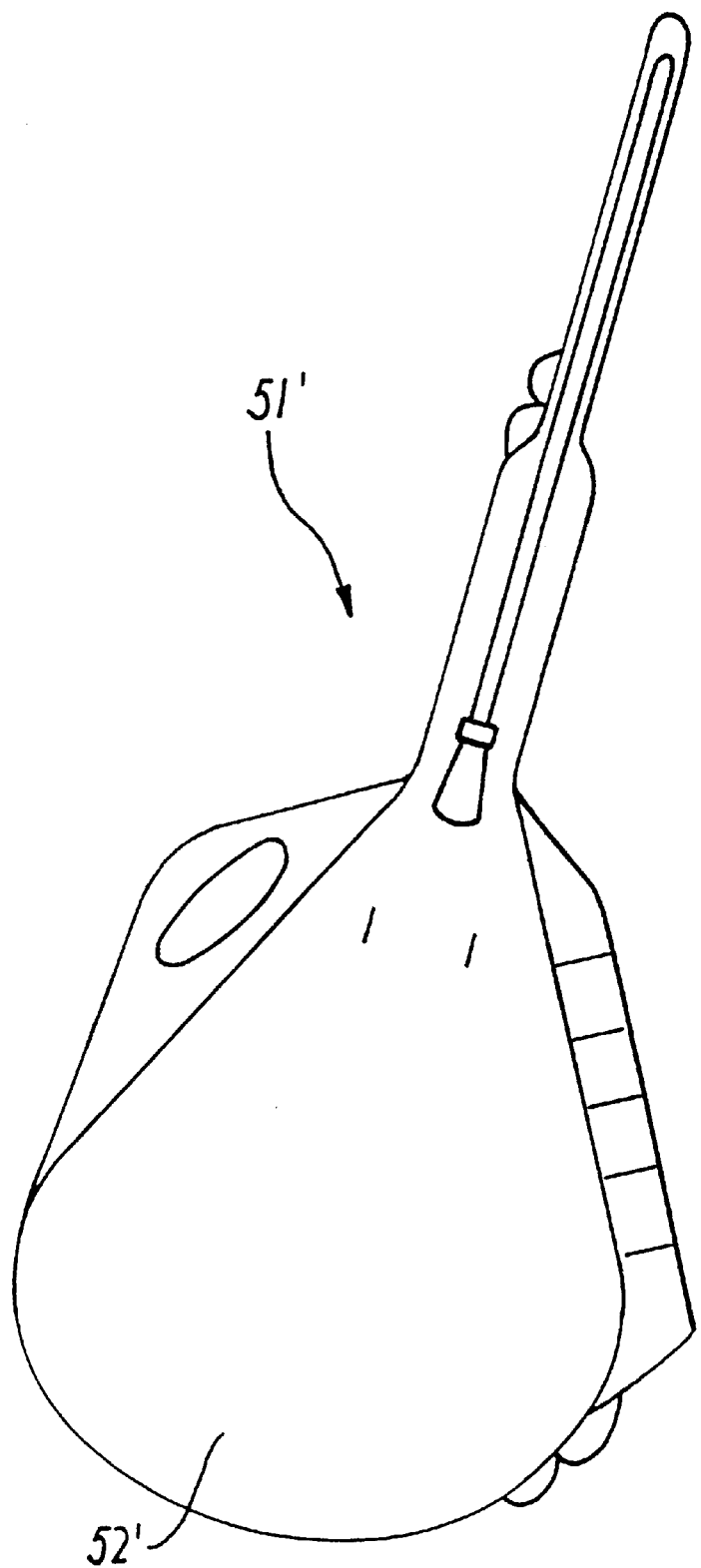
FIG. 5 illustrates a further embodiment.

In the embodiment shown in FIGS. 1 and 2 the urinary catheter assembly of the invention is intended for intermittent catherisation of the bladder of a user and comprises a urinary catheter 1 having a catheter tub 2 with cross-sectional and longitudinal dimensions suitable for introduction of the catheter through the urethra.

The catheter tube 2 extends from a distal inlet end 3, in which urine inlet openings 4 are provided, towards a proximal end, at which the catheter tube is connected with an outlet member 5 designed for connection of the with a hose member (not shown) for transport of urine withdrawn from the bladder to a urine collection bag (not shown).

On a substantial part of its length from the distal end the catheter tube is, in the illustrated embodiment, coated on its external surface with a hydrophilic surface coating 6 of a kind known per se, which by preparation with a liquid swelling medium prior to use of the catheter provides an extreme low friction character of the catheter surface to enable the catheter to slide very easily through the urethra without exposing the urethral walls to any risk of damage. A hydrophilic surface layer may, however, be provided by other means and may include a catheter tube of which the active part to be located in the urethra is made entirely of a hydrophilic material.

The catheter 1 is accommodated in its entirety in a package 7 formed by two sheets 8 and 9 of a gas-impermeable thermoplastic film material such as a multiple layer film material comprising e.g. aluminium, welded together along a welding seam 10 when constitutes a joint defining a cavity 11 narrowly surrounding the catheter tub 2 and a widened end section 12 joining the cavity 11 through a transitional section 13 matching the external dimensions of the outlet or connector member 5.

According to the invention, the hydrophilic surface coating 6 of the catheter 1 is prepared to activate its low friction character prior to arrangement of the catheter 1 in package 7 or immediately following said arrangement before closing the package by treatment with a liquid swelling medium. Since the welding seam 10 is arranged to provide a narrow cavity 11 around the catheter tube 2 the amount of swelling liquid needed for preparation of the hydrophilic coating 6 can be kept low. Experiments have verified that by suitable design of the cavity the amount of swelling liquid may be reduced to a volume of 2 to 50 ml, preferably 2 to 15 ml for female and 5 to 30 ml for male catheters.

To facilitate withdrawal of the prepared catheter 1 from the package 7 the welding joint may, as illustrated in FIG. 3, comprise a part 10a adjacent the distal end of the catheter tube providing a peel-off joint permitting easy separation of plastic film sheets 8 and 9. Thereby, the package 7 itself will serve as an applicator to be gripped by the user to permit introduction of the catheter tube without contamination.

Due to the gas-impermeability of the package 7 the swelling medium may be introduced in the package during the assembling operation prior to completion of the welding and will thereby immediately prepare the hydrophilic coating. The package will itself present the coating from drying out and preserve the low friction character of the surface coating to keep the catheter in a ready to use condition at all times. This would have the inherent advantage that no further preparation step is required prior to use, so that the operation will be reduced to opening of the package 7 for immediate withdrawal of the catheter without the delay resulting from the required preparation period.

Due to the desirability of limiting the amount of swelling liquid, the catheter may be provided with means presenting the swelling liquid from getting into contact with internal or external surface parts of the catheter 1 not provided with the hydrophilic coating 6, during the period needed for preparation of the hydrophilic coating to activate its low friction character. Such means may in a simple manner comprise the application of a film layer 55 of a material soluble by the actual swelling medium to said internal or external surface parts.

As soon in FIG. 4 this may be done in the most simple way by application of such film layers 55 over the catheter inlet openings 4. Thereby, substantially the entire quantity of swelling medium will be effectively used for the preparation of the hydrophilic surface coating.

In FIG. 5 a further embodiment is illustrated in which the catheter package 51 is formed integrally with a urine collecting bag 52. For disabled users like tetraplegics who as described in the foregoing may have severe difficulties in entering available toilet rooms such an integration of the urine collecting bag with the catheter package is a significant practical advantage making the use of the catheter totally independant of the availability of a toilet room. The catheter 1 is located in a relatively narrow tapering part 53 joining the collection bag 52. In this case the catheter 1 will in use not be completely removed from package 51. Instead the distal end of the tapering part 53 may be opened by peel-off separation of two plastic film sheets from which the package 51 is composed. Thereby, the catheter 1 may be introduced by an operation as described above for the embodiment in FIG. 3.

A catheter assembly according to the invention may well comprise a number of catheters packed in individual packages with sufficient gas impermeable properties to last a certain short period, said individual packages being arranged in a common package providing the prescribed long term gas impermeability.

We claim:

1. A urinary catheter assembly comprising at least one urinary catheter (1) having on at least a part of its surface a hydrophillic surface layer (6) intended to produce a low-friction surface character of the catheter by treatment with a liquid swelling medium prior to use of the catheter and a catheter package (7) having a cavity (11) for accommodation of the catheter (1), characterized in that the package (7) is formed with walls made throughout of a gas impermeable material for long time accommodation of said at least one urinary catheter, said catheter having been pretreated with said liquid swelling medium before arrangement in said package for long time preservation of said low-friction surface character during accommodation in said package and provision of a ready-to-use catheter assembly.

2. A urinary catheter assembly as claimed in claim 1, characterized in that the catheter package (7) is formed from two sheets (8, 9) of gas impermeable film material connected with each other by a gas impermeable joint (10) defining the cavity (11) for accommodating the catheter (1).

3. A urinary catheter assembly as claimed in claim 2, characterized in that the catheter package (7) is of a general elongate shape with said joint (10) arranged to define said cavity (11) to accommodate the catheter (1) in a substantially linear orientation.

4. A urinary catheter assembly as claimed in claim 2, characterized in that said joint (10) is arranged to provide said cavity (11) with a cross-section narrowly surrounding the catheter (1).

5. A urinary catheter assembly as claimed in claim 2, characterized in that said joint (10) is a welding joint.

6. A urinary catheter assembly as claimed in claim 5, characterized in that said welding joint (10) comprises a part (10*a*) at the end of the package remote from a compartment (12) providing a peel-off joint to separate said sheets (8, 9) from each other for withdrawal of said catheter (1) from the package (7).

7. A urinary catheter assembly as claimed in claim 1, characterized in that the catheter (1) is provided with means preventing said swelling medium from getting into contact with internal or external surface parts of the catheter not provided with said hydrophillic coating (6) for an activation period during which said medium is applied to the surface part provided with said hydrophillic coating (6).

8. A urinary catheter assembly as claimed in claim 7, characterized in that said means comprises a film layer (55) of a material soluble by said swelling medium applied to said parts not provided with said hydrophillic coating.

9. A urinary catheter assembly as claimed in claim 1, characterized in that said package includes a bag (52) communicating with the catheter (1) for collection of urine.

10. A urinary catheter assembly as claimed in claim 1, characterized in that said liquid swelling medium is selected from the group consisting of aqueous solution, an isotonic aqueous solution, as isotonic aqueous solution of sodium chloride and sterile water.

* * * * *